(12) United States Patent
Hatase et al.

(10) Patent No.: US 11,659,981 B2
(45) Date of Patent: May 30, 2023

(54) ENDOSCOPE WITH A HOLDER INCLUDING A LENS AND AN IMAGE SENSOR

(71) Applicant: Panasonic i-PRO Sensing Solutions Co., Ltd., Fukuoka (JP)

(72) Inventors: Yuichi Hatase, Fukuoka (JP); Naoyuki Haraguchi, Saga (JP)

(73) Assignee: I-PRO CO., LTD., Tokyo (JP)

( * ) Notice: Subject to any disclaimer, the term of this patent is extended or adjusted under 35 U.S.C. 154(b) by 565 days.

(21) Appl. No.: 16/508,050

(22) Filed: Jul. 10, 2019

(65) Prior Publication Data

US 2020/0015664 A1    Jan. 16, 2020

(30) Foreign Application Priority Data

Jul. 13, 2018  (JP) .............................. JP2018-133077
Jul. 13, 2018  (JP) .............................. JP2018-133078

(51) Int. Cl.
*A61B 1/01*    (2006.01)
*A61B 1/05*    (2006.01)
(Continued)

(52) U.S. Cl.
CPC ............ *A61B 1/01* (2013.01); *A61B 1/00096* (2013.01); *A61B 1/05* (2013.01); *A61B 1/07* (2013.01);
(Continued)

(58) Field of Classification Search
CPC ............ A61B 1/00096; A61B 1/00126; A61B 1/00165; A61B 1/05; A61B 1/07;
(Continued)

(56) References Cited

U.S. PATENT DOCUMENTS 4,960,106 A * 10/1990 Kubokawa ........... A61B 1/0008
600/116
5,035,231 A    7/1991 Kubokawa et al.
(Continued)

FOREIGN PATENT DOCUMENTS

JP    63-270022 A    11/1988
JP    1-101957 A    4/1989
(Continued)

OTHER PUBLICATIONS

Japanese Notice of Reasons for Refusal, dated Mar. 15, 2022, for Japanese Application No. 2018-133077, 6 pages, (with English translation).
(Continued)

*Primary Examiner* — Aaron B Fairchild
*Assistant Examiner* — Julianna J Nicolaus
(74) *Attorney, Agent, or Firm* — Seed IP Law Group LLP

(57) ABSTRACT

A front end of an endoscope includes both a lens and an image sensor. There is provided a guide wire hole. The endoscope is easily inserted along a guide wire while a diameter is reduced in the front end in an insertion direction. The endoscope includes a lens which is disposed in the front end in the insertion direction, and receives incident imaging light, an image sensor disposed in a rear portion of the lens, and on which an image of the imaging light is formed, a holder which covers the lens and the image sensor, and having the guide wire hole through which the guide wire penetrates, and a flexible tubular sheath connected to a rear end portion of the holder, and into which a cable conductively connected to the image sensor is inserted.

10 Claims, 16 Drawing Sheets

(51) Int. Cl.
*A61B 1/00* (2006.01)
*A61B 1/07* (2006.01)
*H04N 23/51* (2023.01)
*H04N 23/54* (2023.01)
*H04N 23/55* (2023.01)
*H04N 23/50* (2023.01)

(52) U.S. Cl.
CPC ............ *H04N 23/51* (2023.01); *H04N 23/54* (2023.01); *H04N 23/55* (2023.01); *H04N 23/555* (2023.01)

(58) Field of Classification Search
CPC .. H04N 5/2252; H04N 5/2253; H04N 5/2256; H04N 2005/2255
See application file for complete search history.

(56) References Cited

U.S. PATENT DOCUMENTS

| | | | | |
|---|---|---|---|---|
| 5,643,175 | A | * | 7/1997 | Adair ................. A61B 1/00073 600/123 |
| 2002/0183591 | A1 | | 12/2002 | Matsuura et al. |
| 2004/0230097 | A1 | * | 11/2004 | Stefanchik ......... A61B 1/00073 600/104 |
| 2014/0148647 | A1 | | 5/2014 | Okazaki |
| 2016/0195706 | A1 | * | 7/2016 | Fujii .................... G02B 6/0008 362/551 |
| 2016/0238832 | A1 | | 8/2016 | Sasamoto |
| 2019/0387966 | A1 | * | 12/2019 | Tsuruta .................... A61B 1/01 |

FOREIGN PATENT DOCUMENTS

| | | |
|---|---|---|
| JP | 2001-128937 A | 5/2001 |
| JP | 2002-306398 A | 10/2002 |
| JP | 2013-034498 A | 2/2013 |
| JP | 2013-198566 A | 10/2013 |
| JP | 3188206 U | 1/2014 |
| JP | 2016-083009 A | 5/2016 |
| WO | 2013/018917 A1 | 2/2013 |
| WO | 2015/064614 A1 | 5/2015 |

OTHER PUBLICATIONS

Japanese Notice of Reasons for Refusal, dated Mar. 15, 2022, for Japanese Application No. 2018-133078, 9 pages, (with English translation).

* cited by examiner

ENDOSCOPE WITH A HOLDER INCLUDING A LENS AND AN IMAGE SENSOR

BACKGROUND OF THE INVENTION

1. Field of the Invention

The present disclosure relates to an endoscope.

2. Description of the Related Art

A thinned vascular endoscope catheter is known which enables a smooth access to a lesion by using a guide wire inserted in advance into a blood vessel and having an outer diameter of approximately 0.35 mm (for example, refer to Japanese Registered Utility Model No. 3188206 as Patent Reference 1). In the thinned vascular endoscope catheter, a main body thereof is an optical fiber bundle having an outer diameter of approximately 0.4 mm, and a front end thereof includes a chip having a circular shape in cross section and an optical lens. The chip has a guide wire passing lumen, and is provided with a guide wire. The thinned vascular endoscope catheter can be easily inserted into a target site along the guide wire by allowing the guide wire to penetrate through the guide wire passing lumen. In the thinned vascular endoscope catheter, an intravascular image is captured by the optical lens, and is transmitted to a proximal end side via the optical fiber bundle. The transmitted image can be displayed on a display device.

Patent Reference 1: Japanese Registered Utility Model No. 3188206

SUMMARY OF THE INVENTION

However, according to a configuration of the thinned vascular endoscope catheter disclosed in Japanese Registered Utility Model No. 3188206, a chip (that is, a holder) is further inserted from the outside into an outer periphery of a sheath which protects the outside of the optical fiber bundle. Therefore, a thickness of the chip (that is, the holder) is added to a thickness of the sheath in an outer diameter of a front end portion of the thinned vascular endoscope catheter, and the outer diameter of the front end portion increases, thereby causing a problem in that size reduction is less likely to be achieved.

The present disclosure is devised in view of the above-described circumstances in the related art, and aims to provide an endoscope whose front end has both a lens and an image sensor, which includes a guide wire hole, and which can be easily inserted along a guide wire while a diameter can be reduced in the front end in an insertion direction.

According to the present disclosure, there is provided an endoscope including a lens which is disposed in a front end in an insertion direction into a test object, and receives an incident imaging light, an image sensor which is disposed in a rear end of the lens, and in which an image of the imaging light is formed on the image sensor, a holder which covers the lens and the image sensor, and includes a guide wire hole through which a guide wire to be inserted into the test object penetrates, and a flexible tubular sheath connected to a rear end portion of the holder, and into which a cable conductively connected to the image sensor is inserted.

According to the present disclosure, the front end of the endoscope has both the lens and the image sensor. The endoscope is provided with the guide wire hole. The endoscope can be easily inserted along the guide wire while a diameter can be reduced in the front end in the insertion direction.

DETAILED DESCRIPTION OF THE EXEMPLARY EMBODIMENTS

Hereinafter, an embodiment specifically disclosing an endoscope according to the present disclosure will be described in detail with reference to the drawings as appropriate. Unnecessarily detailed description may be omitted in some cases. For example, detailed description of well-known items or repeated description of substantially the same configuration may be omitted in some cases. The reason is to avoid the following description from being unnecessarily redundant, and to facilitate understanding of those skilled in the art. The accompanying drawings and the following description are provided in order to enable those skilled in the art to fully understand the present disclosure, and are not intended to limit a gist disclosed in the appended claims.

Figure 1:
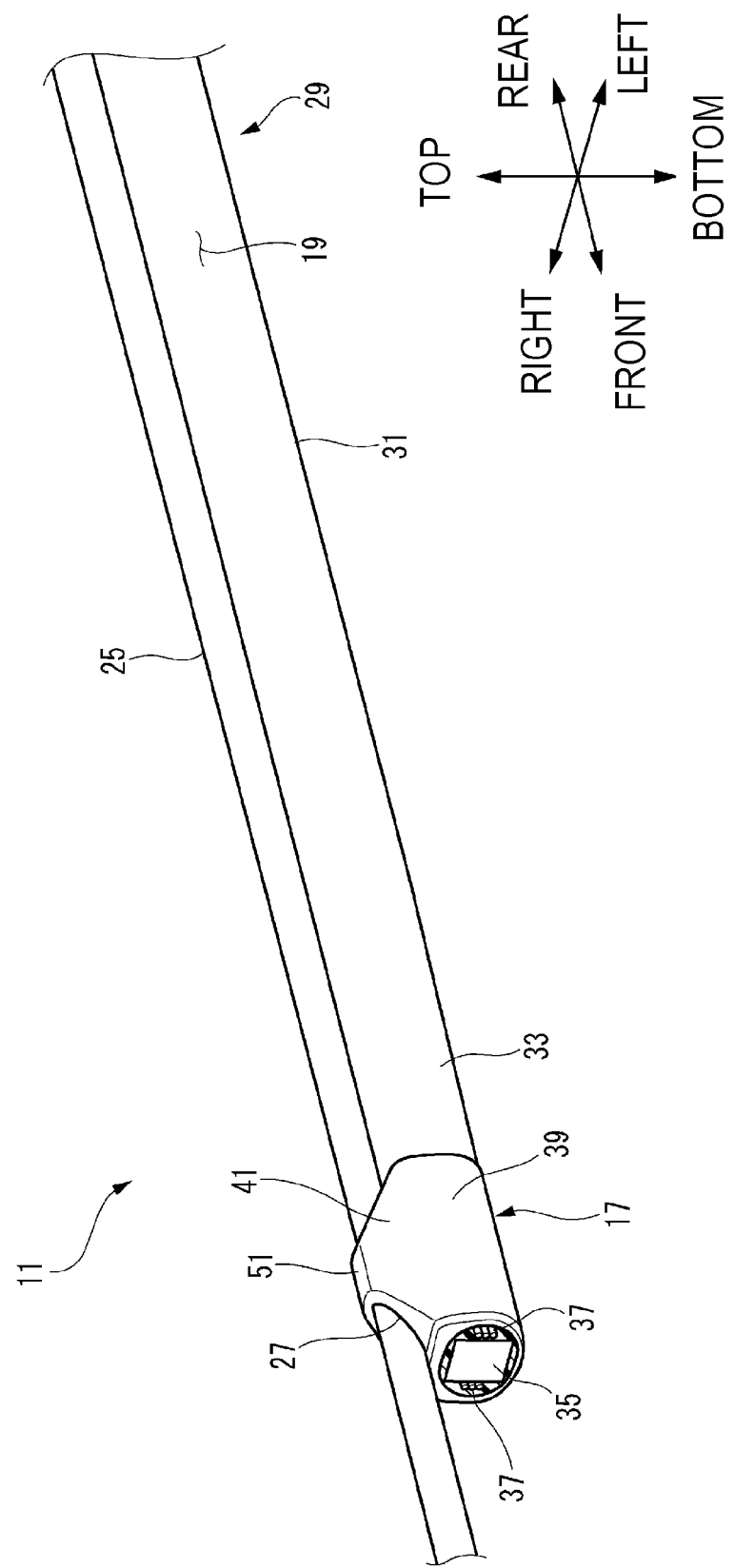
FIG. 1 is a perspective view illustrating an exterior example of a front end in an insertion direction side of an endoscope according to Embodiment 1.

FIG. 1 is a perspective view illustrating an exterior example of a front end in an insertion direction side of an endoscope 11 according to Embodiment 1. In the following description, directions used in the description are based on directions illustrated in FIG. 1.

Here, in upward and downward directions illustrated in FIG. 1, rightward and leftward directions are set when an operator faces forward from the front end in the insertion direction of the endoscope 11. A right hand side of the operator corresponds to the rightward direction, and a left hand side corresponds to the leftward direction.

Figure 8:
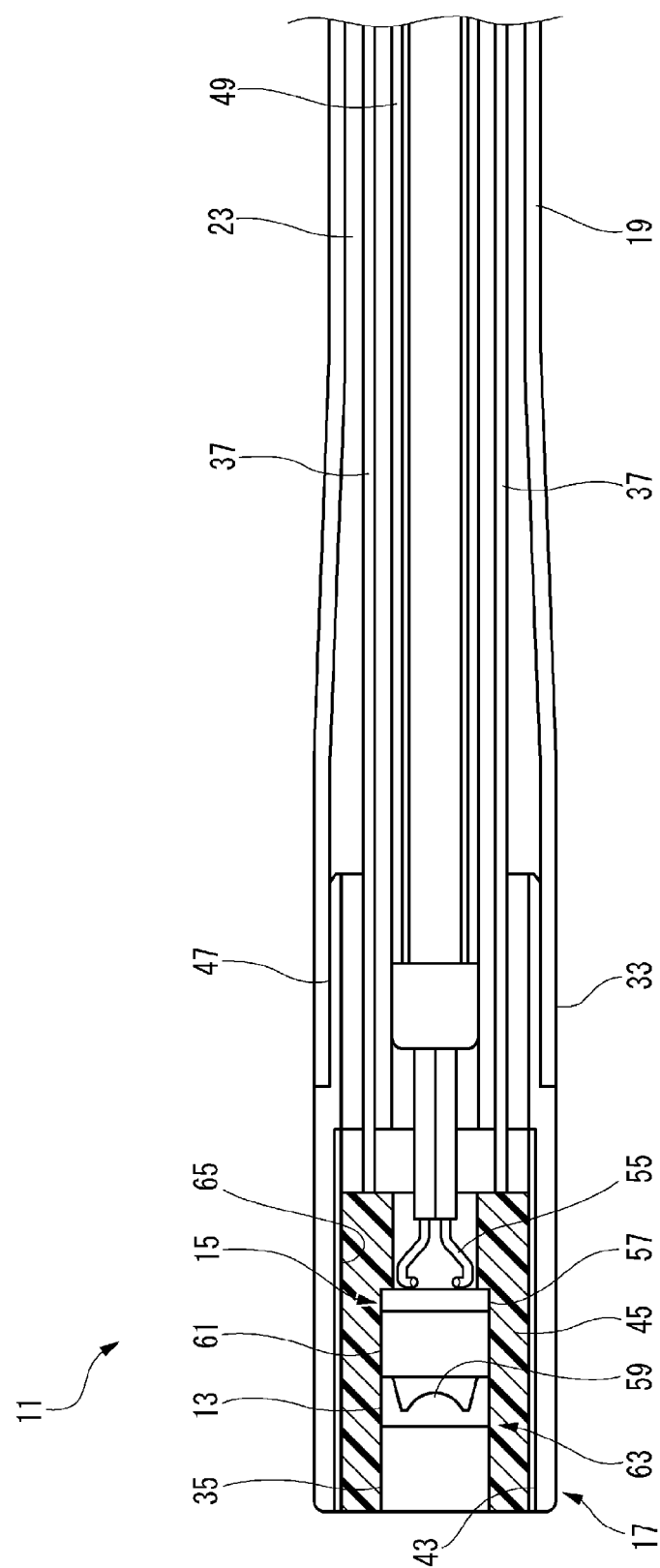
FIG. 8 is a sectional view taken along line A-A in FIG. 4.
Figure 9:
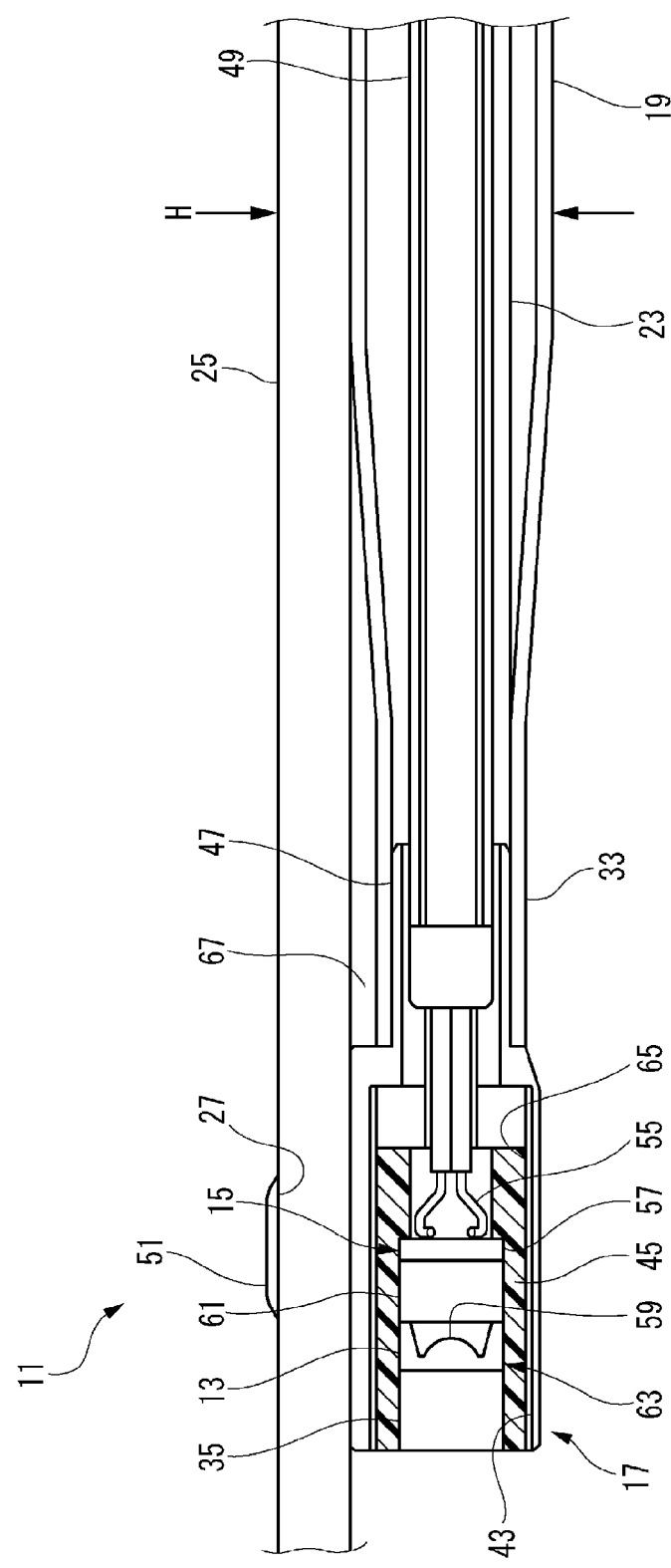
FIG. 9 is a sectional view taken along line B-B in FIG. 4.

As a main configuration, the endoscope 11 according to Embodiment 1 includes a lens 13 (refer to FIG. 8), an image sensor 15 (refer to FIG. 8), a holder 17, a sheath 19, a conductive member (for example, a metal cylinder portion 21 in FIG. 11), and a grounding member (a metal wire 23 in FIG. 9).

For example, when a surgical operation or an examination is performed, the endoscope 11 can be used by being inserted into a guide catheter (not illustrated) to be inserted so as to house a guide wire 25 after the guide wire 25 is inserted into a test object (for example, a human body). For example, the guide catheter is inserted into a blood vessel inside the test object. As a specific dimension example, the guide catheter has an outer diameter of 1.7 to 1.8 mm and an inner diameter of 1.5 mm, for example. The guide catheter has an outer diameter of 1.7 mm in this embodiment. The guide wire 25 penetrates through the guide catheter. The guide wire 25 has the outer diameter of 0.35 mm, for example. The endoscope 11 together with the guide wire 25 penetrates through the guide catheter. Therefore, the endoscope 11 includes a guide wire hole 27 for allowing the guide wire 25 to penetrate therethrough. The endoscope 11 according to Embodiment 1 includes a guide wire hole 27, and is allowed to penetrate through the guide catheter. Accordingly, a maximum outer diameter D (refer to FIG. 3) is set to 1.35 mm or smaller, for example.

In the endoscope 11, the holder 17 is disposed in the front end in the insertion direction of an insertion portion 29. The insertion portion 29 is covered by the sheath 19 almost in full length. For example, the sheath 19 is formed of a flexible resin material in a tubular shape (that is, in a tube shape). For example, in order to strengthen the sheath 19, an inner peripheral side of the sheath 19 can be provided with a single-wire, a multi-wire, or a braided tensile strength wire. Examples of the tensile strength wire include aramid fibers such as poly-p-phenylene terephthalamide fibers, polyarylate fibers, polyparaphenylene benzbisoxazole fibers, polyester fibers such as polyethylene terephthalate fibers, nylon fibers, thin tungsten wires, or thin stainless steel wires. The sheath 19 is a perfect circle portion 31 whose cross-sectional shape in a direction perpendicular to an axis line or an optical axis of the lens 13 is a perfect circle. However, in order to have flexibility, a sheath front end serving as a connection portion connected to the holder 17 is fitted by deforming as will be described later. In this manner, the cross-sectional shape serves as a flat portion 33 having an elliptical shape.

The holder 17 to which the sheath 19 is connected exposes a lens cover glass 35 on the front end surface. The lens 13 serving as an imaging light system may have the lens cover glass 35 integrally fixed to the surface. According to Embodiment 1, the lens cover glass 35 integrally fixed to the lens 13 is exposed on the front end surface of the holder 17. The lens 13 receives imaging light by being disposed in the front end in the insertion direction (that is, light reflected from a subject such as a lesion inside the test object is incident thereon). On the front end surface of the holder 17, a light emitting end surface having a plurality of lighting optical fibers 37 arrayed in succession in an upward-downward direction are arranged on the right and left across the lens cover glass 35.

The holder 17 has a ridge portion 41 on an upper side of a flat column portion 39 having an elliptical shape laterally having a major axis. The guide wire hole 27 is drilled in the ridge portion 41 while penetrating in an extension direction of the sheath 19. The holder 17 covers the lens 13 and the image sensor 15 which configure the front end portion of the endoscope 11, and is configured to include the guide wire hole 27 penetrating the guide wire 25.

Figure 2:
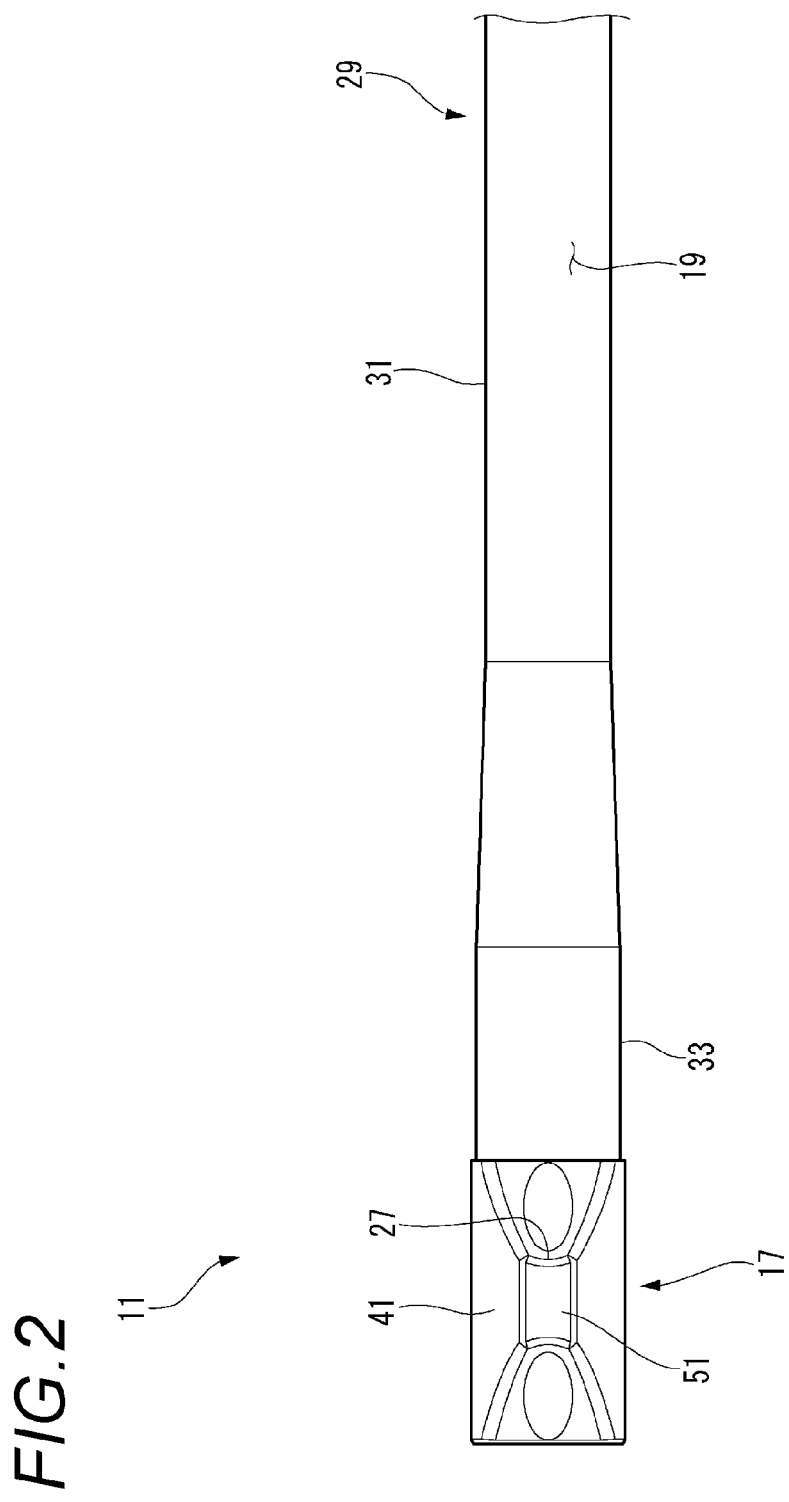
FIG. 2 is a plan view of the endoscope illustrated in FIG. 1.

FIG. 2 is a plan view of the endoscope 11 illustrated in FIG. 1. The sheath 19 is the flat portion 33 which is wider in a rightward-leftward direction than the perfect circle portion 31 in the sheath front end (that is, the front end portion of the sheath 19). That is, the sheath 19 has an outer shape of the flat portion 33 in the sheath front end (refer to the description above). However, the flat portion 33 converges from the sheath front end toward the rear end side, and the sheath 19 has an outer shape of the perfect circle portion 31. The holder 17 is slightly larger in the rightward-leftward direction than the flat portion 33. However, the holder 17 may be formed to have the same width as the flat portion 33. The guide wire hole 27 is drilled in a top portion in a central portion in a direction along an axis line of the holder 17 in the ridge portion 41.

Figure 3:
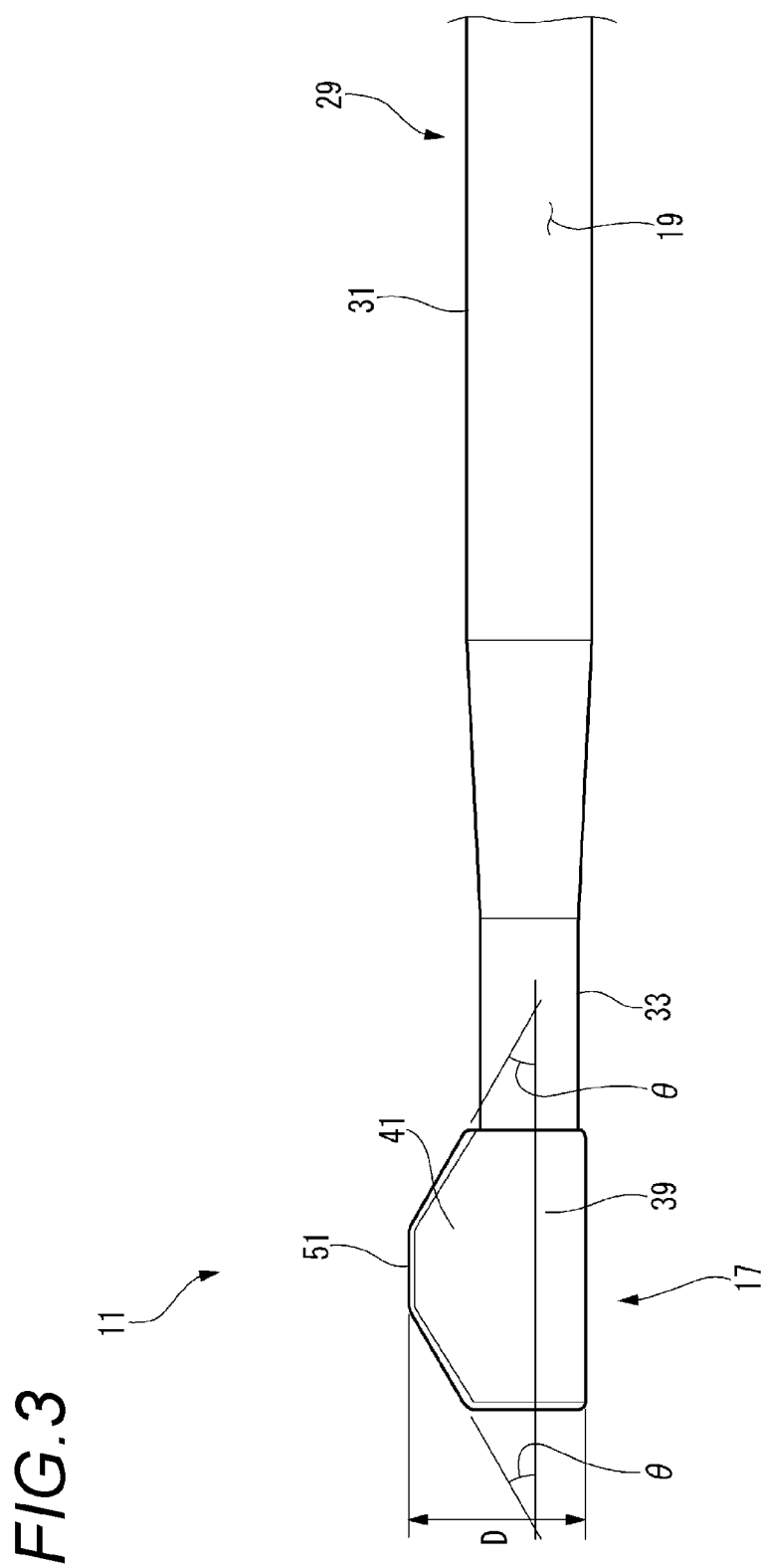
FIG. 3 is a side view of the endoscope illustrated in FIG. 1.

FIG. 3 is a side view of the endoscope 11 illustrated in FIG. 1. In the holder 17, the ridge portion 41 has a mountain shape. In the endoscope 11 according to Embodiment 1, a total height to the top portion of the holder 17 is set to the above-described maximum outer diameter D (that is, the maximum outer diameter of the endoscope 11). An inclination angle θ of the mountain shape in the front end in the insertion direction side is the same as that in the rear end in the insertion direction side. The inclination angle θ is formed so that a nipping angle with the axis line of the holder 17 is approximately 30 degrees. In this manner, the endoscope 11 can be smoothly inserted into and removed from a blood vessel or a catheter. The inclination angle is not limited to an angle value described above, and the inclination angle θ of the mountain shape in the front end in the insertion direction side may not be the same as that in the rear end in the insertion direction side.

Figure 4:
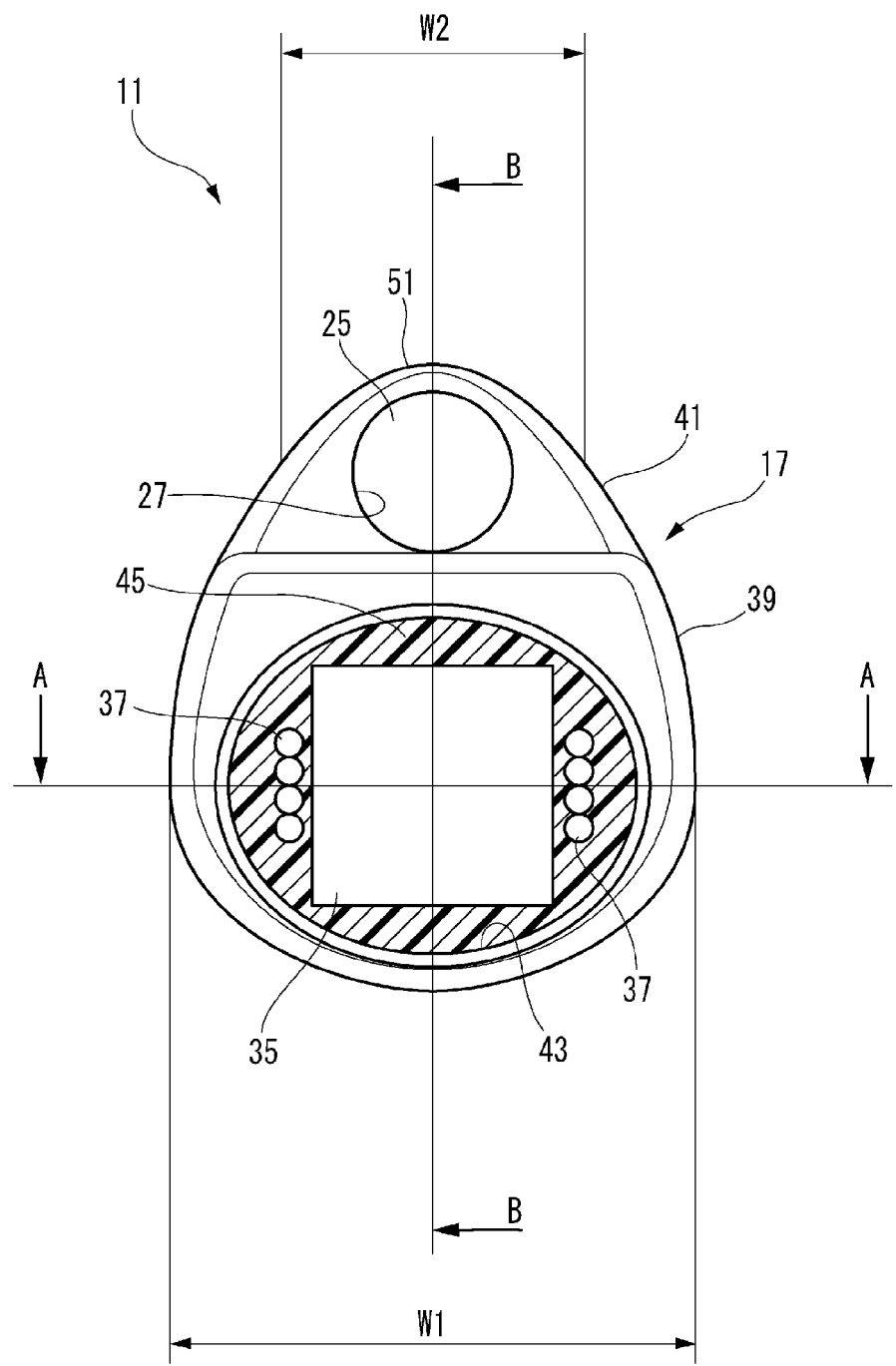
FIG. 4 is a front view of the endoscope illustrated in FIG. 1.

FIG. 4 is a front view of the endoscope 11 illustrated in FIG. 1. The front end surface of the holder 17 has only two holes including the guide wire hole 27 and an observation hole 43 for arranging the lens cover glass 35 and the lighting optical fiber 37. The lens cover glass 35 and the lighting optical fiber 37 which are arranged inward of the observation hole 43 are stably fixed by a black resin 45 filling the observation hole 43.

In a front view of the front end surface the guide wire hole 27 and the observation hole 43 are arranged up and down, the holder 17 is formed so that a lateral width W2 across the guide wire hole 27 is narrower than a lateral width W1 across the observation hole 43. In this manner, an outer shape of the holder 17 in a front view becomes a so-called teardrop shape. A clear liquid is caused to flow into a gap between the catheter or the blood vessel and the endoscope 11. Therefore, a visual field is easily maintained.

Figure 5:
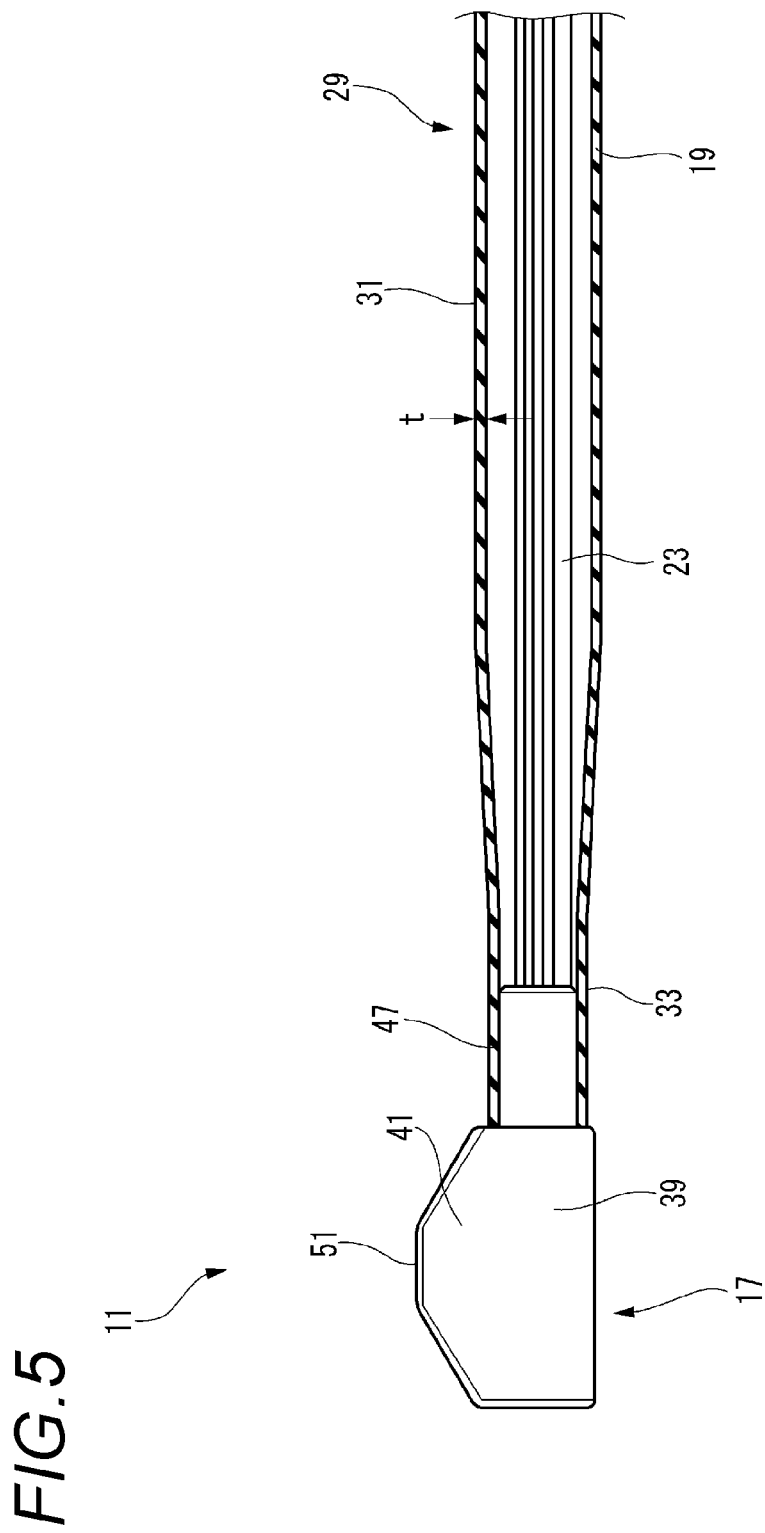
FIG. 5 is a side view illustrating a cut out sheath in FIG. 3.

FIG. 5 is a side view of the cut out sheath 19 in FIG. 3. The holder 17 has a cylindrical sheath fitting portion 47 protruding rearward from the rear end of the flat column portion 39 (example of the camera housing). The sheath front end is fitted and connected to an outer periphery of the sheath fitting portion 47. In the holder 17, the flat column portion 39, the ridge portion 41, and the sheath fitting portion 47 are integrally formed of metal. As the metal, for example, SUS (stainless steel) can be used. The sheath 19 is formed to have a thickness t of 75 µm, for example. The sheath 19 is connected to the sheath fitting portion 47 extending from the rear end portion of the holder 17. The cable 49 or the lighting optical fiber 37 conductively connected to the image sensor 15 is inserted into the sheath 19.

Figure 6:
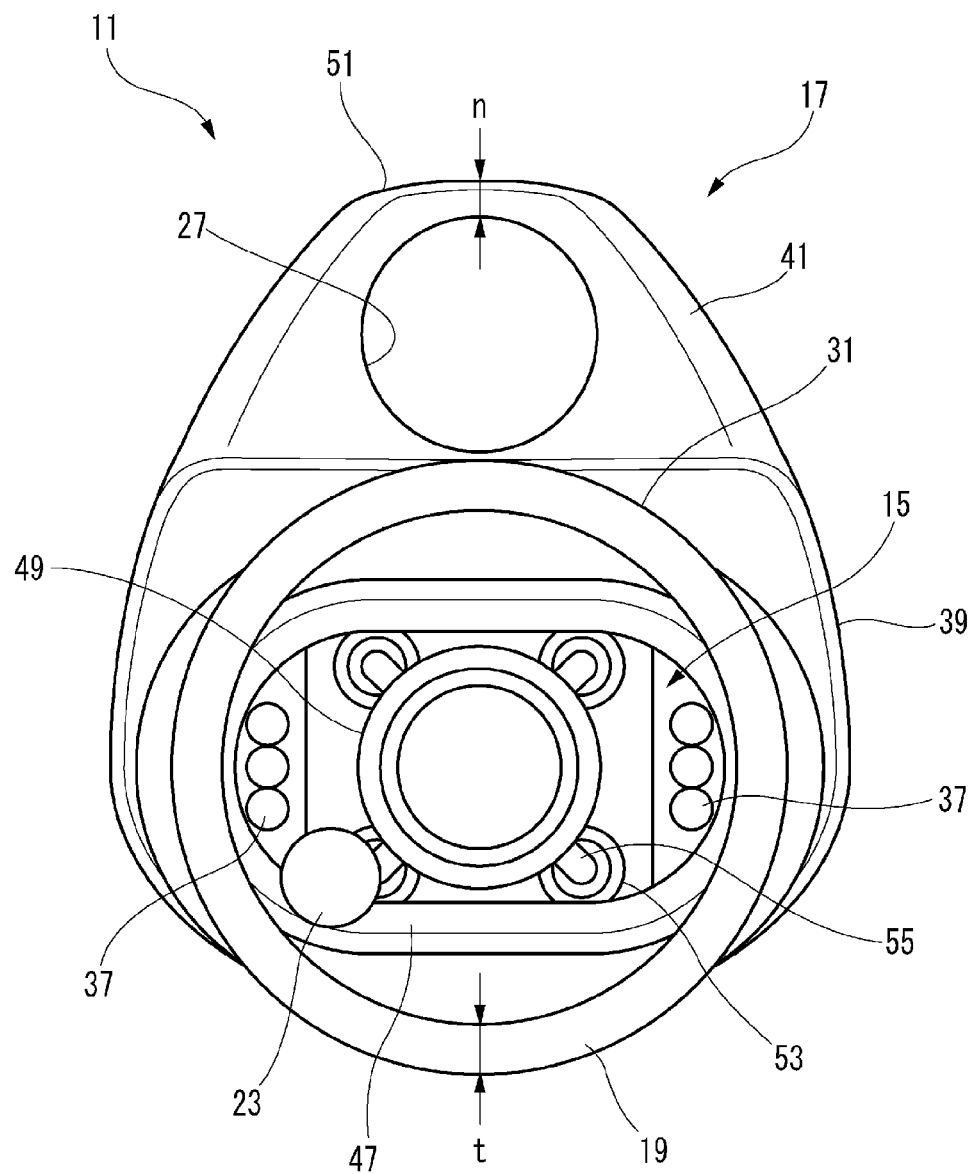
FIG. 6 is a rear view when a holder is viewed from a cross section of a perfect circle portion of the sheath.

FIG. 6 is a rear view when the holder 17 is viewed from a cross section of the perfect circle portion 31 of the sheath 19. The rear end in the insertion direction of the sheath 19 is the perfect circle portion 31. The sheath 19 gradually deforms in a flat shape toward the sheath fitting portion 47, and forms an elliptical shape along the outer periphery of the sheath fitting portion 47 in a fitting portion fitted to the sheath fitting portion 47. The perfect circle portion 31 is almost in contact with the guide wire hole 27. The guide wire hole 27 is drilled in the ridge portion 41 while leaving a bridge portion 51 in the top portion. A thickness n of the bridge portion 51 is set to 50 μm, for example.

The image sensor 15 is visible inside the sheath fitting portion 47. For example, a rear surface of the image sensor 15 has four the bumps 53. In each of the bumps 53, a plurality of core wires 55 bundled as a cable 49 are fixed to each other by means of soldering. In this manner, in the image sensor 15, the cable 49 and a sensor circuit unit 57 (refer to FIG. 15) are conductively connected to each other. In the sheath 19, a grounding member penetrates the sheath 19 along the cable 49. The grounding member is conductively connected to the sheath fitting portion 47 of the holder 17.

Figure 7:
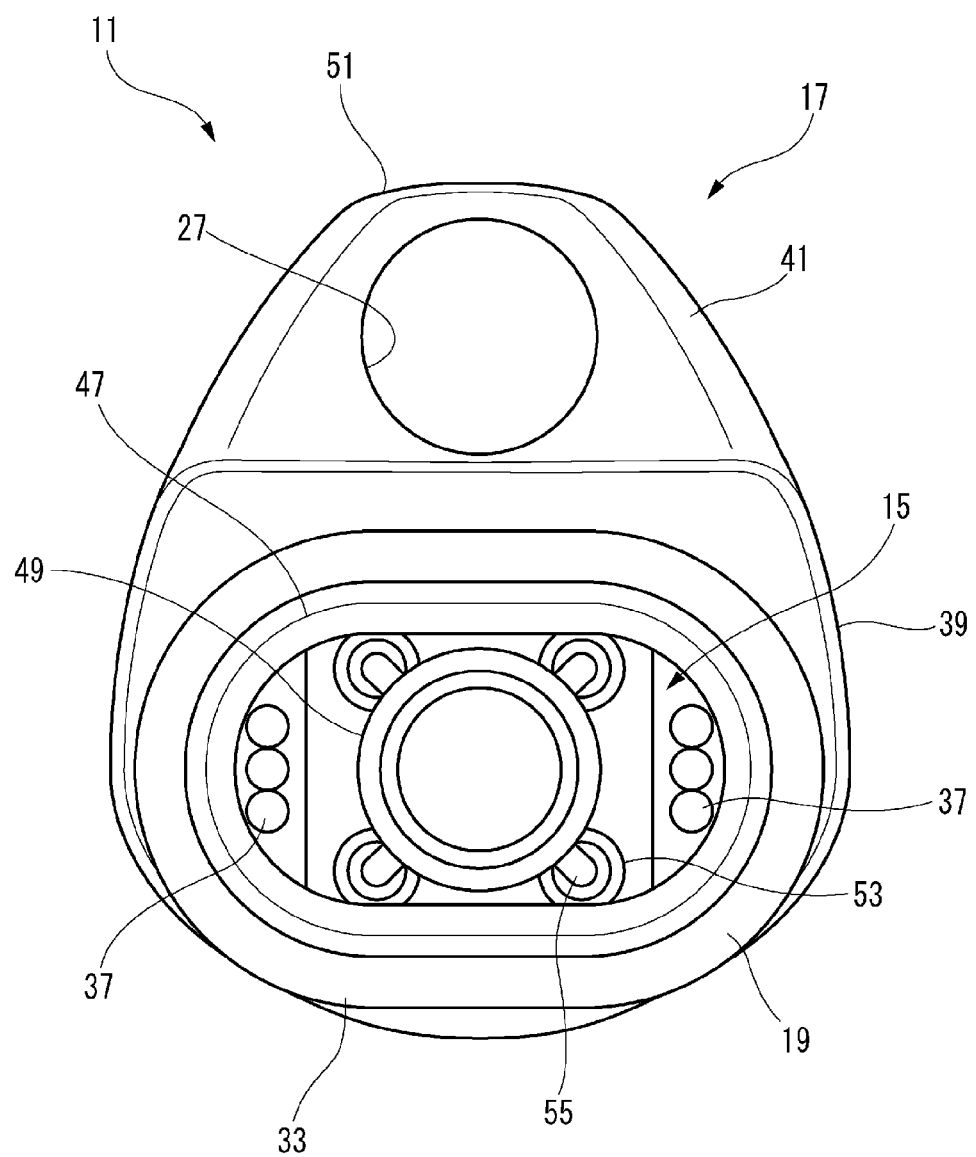
FIG. 7 is a rear view when the holder is viewed from a cross section of an ellipse portion of the sheath.

FIG. 7 is a rear view when the holder 17 is viewed from a cross section of an ellipse portion of the sheath 19. The sheath fitting portion 47 protruding rearward from the holder 17 is formed in an elliptical cylinder shape in which the cross-sectional shape in a direction perpendicular to the axis line of the sheath 19 has one end of a minor axis of the sheath 19 close to the guide wire hole 27. An annular portion interposed between the cross section of the sheath 19 in FIG. 7 and the end surface of the sheath fitting portion 47 is an inner wall surface of the sheath 19 which is continuous while gradually decreasing in diameter toward the sheath fitting portion 47.

FIG. 8 is a sectional view taken along line A-A in FIG. 4. In the endoscope 11, the lens cover glass 35 and the lens 13 are formed in the same outer shape by using a short flat square pole (for example, a regular square pole) in an axial direction. In the lens 13, a concave portion is formed on a side opposite to the lens cover glass 35. A bottom surface of the concave portion in the lens 13 has a convex lens surface 59 facing the image sensor 15. The convex lens surface 59 is located facing the image sensor 15 via air, and functions as an effective element portion (that is, a portion for refracting incident light) of the lens 13.

In the image sensor 15, a surface facing the lens 13 is a light receiving surface. The image sensor 15 is disposed in a rear portion of the lens 13. Accordingly, an image of the imaging light is formed on the light receiving surface. In the image sensor 15, a sensor cover glass 61 is integrally fixed to the light receiving surface. The image sensor 15 is integrated with the sensor cover glass 61, thereby ensuring strength. The lens cover glass 35, the lens 13, the sensor cover glass 61, and the image sensor 15 configure an imaging unit 63.

FIG. 9 is a sectional view taken along line B-B in FIG. 4. The holder 17 internally has a camera housing 65. The camera housing 65 houses the imaging unit 63. The camera housing 65 is formed inward of the above-described flat column portion 39. In the holder 17, the sheath front end is connected to the sheath fitting portion 47 extending from the rear end of the camera housing 65. The endoscope 11 is almost in contact with the guide wire 25 in the perfect circle portion 31 of the sheath 19. In the endoscope 11, a total height H including the guide wire 25 in the perfect circle portion 31 is approximately in a range of 1.2 to 1.35 mm, for example. The total height H is approximately 1.3 mm in this embodiment.

The endoscope 11 deforms into a horizontally long elliptical shape by fitting the sheath 19 to the sheath fitting portion 47, below the guide wire 25 penetrating through the guide wire hole 27. In this manner, the endoscope 11 has a gap 67 formed between the guide wire 25 and the sheath 19 in the front end in the insertion direction.

The endoscope 11 includes a conductive member for covering the lens 13 and the image sensor 15. The conductive member is grounded to the ground (GND) via a grounding member. In Embodiment 1, the conductive member is the holder 17.

In Embodiment 1, the grounding member is the metal wire 23. The metal wire 23 extends along the cable 49 in the sheath 19. The metal wire 23 is connected to an insulation earth portion of an insulated circuit disposed in a video processor (not illustrated) to which the endoscope 11 is connected, via a plug portion (not illustrated) whose proximal end is connected to the insertion portion 29.

In the endoscope 11, the whole holder 17 formed of metal can serve as an application target of static electricity. In the endoscope 11, for example, when a surgical operation or an examination is performed, the static electricity is applied to the holder 17. A current flowing from the holder 17 to the metal wire 23 is released to the insulation earth portion of the insulated circuit via the plug portion. In this manner, the static electricity is prevented from being applied to the sensor circuit unit 57 of the image sensor 15.

For example, it is necessary to consider that the endoscope 11 used as a medical endoscope has to prevent a leakage current from flowing into a patient who is a test object. Therefore, the metal wire 23 for inducing the static electricity and the holder 17 serving as a patient contact portion may be insulated by providing a gap G (refer to FIG. 16). The metal wire 23 for inducing the static electricity is connected to the insulation earth portion in which the leakage current is sufficiently reduced via an electrical insulation circuit. In this way, in the endoscope 11, the metal wire 23 for inducing and releasing the static electricity is installed between the holder 17 and the endoscope 11, thereby releasing the static electricity to the insulation earth portion. The endoscope 11 includes a configuration in this way. Accordingly, a problem inherent to an electronic endoscope having the image sensor 15 mounted on the front end is solved, and the image sensor 15 is protected so that the static electricity does not flow into the patient.

Alternatively, the conductive member may be directly and conductively connected to the grounding member without providing the gap G. In this case, a protective element such as an electro static discharge (ESD) suppressor is disposed between the metal wire 23 and the GND.

Figure 10:
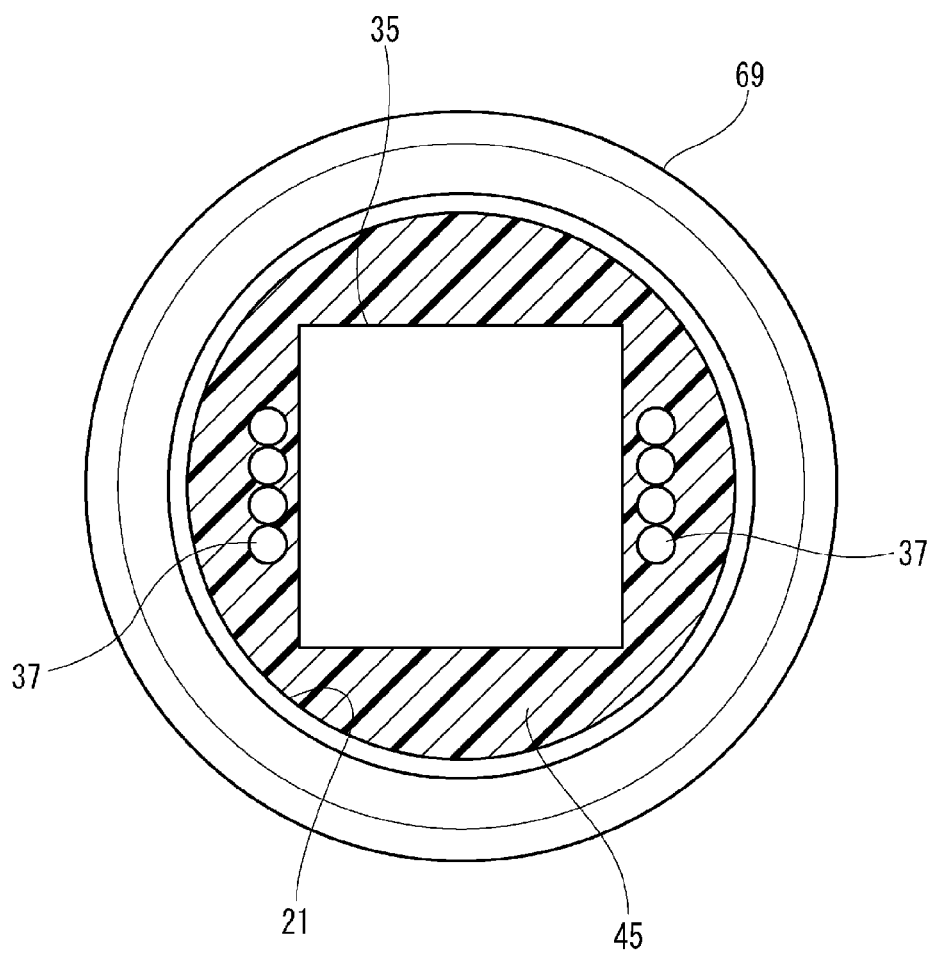
FIG. 10 is a front view of a holder according to another configuration example.

FIG. 10 is a front view of a holder 69 according to another configuration example. In this configuration example, the holder 69 is not provided with the guide wire hole 27. A configuration including the conductive member and the grounding member in the front end in the insertion direction is also useful for the endoscope adopting a structure having no guide wire hole 27 as illustrated in FIG. 10. In this case, for example, the holder 69 is formed in a cylindrical shape. The holder 69 may be made of metal or a resin. In a case where the holder 69 is made of the resin, the metal cylinder portion 21 serving as a rigid conductive member is disposed inward of the holder 69. For example, the metal cylinder portion 21 can have the thickness of 30 to 50 μm.

Figure 11:
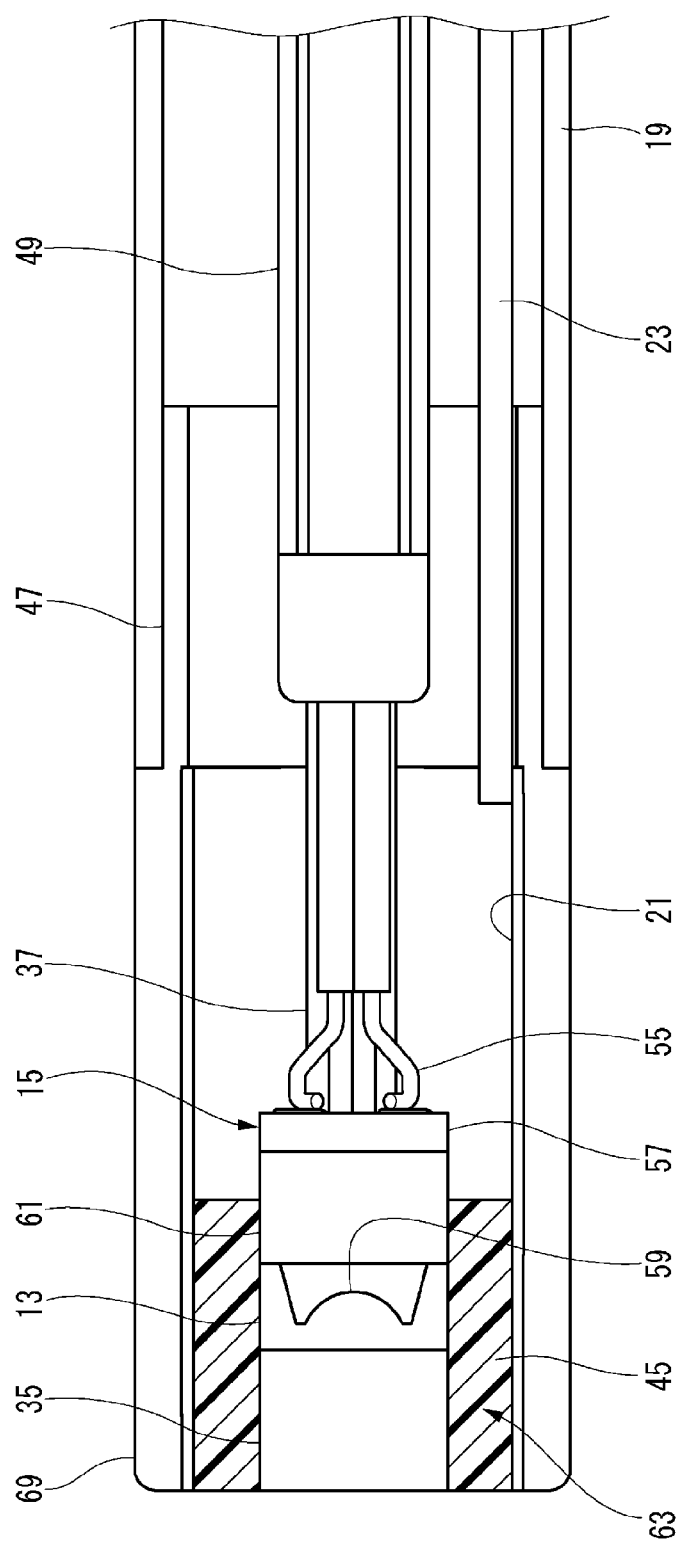
FIG. 11 is a side sectional view of the holder illustrated in FIG. 10.

FIG. 11 is a side sectional view of the holder 69 illustrated in FIG. 10. The metal cylinder portion 21 internally houses the imaging unit 63. In the imaging unit 63, for example, the lens cover glass 35, the lens 13, and a portion of the sensor cover glass 61 are stably fixed to the inner periphery of the metal cylinder portion 21 by using the black resin 45. In the metal cylinder portion 21, the rear end sufficiently separated from the image sensor 15 of the imaging unit 63 is connected to the metal wire 23.

Figure 12:
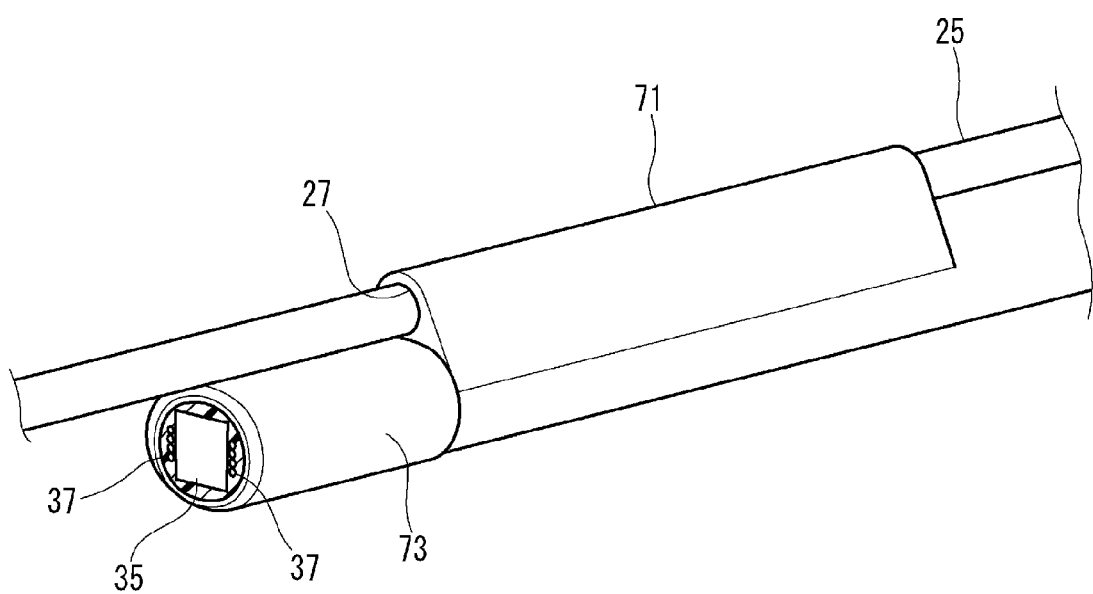
FIG. 12 is a perspective view illustrating another configuration example having a lumen tube as a guide wire lumen.

FIG. 12 is a perspective view of another configuration example having a lumen tube 71 as a guide wire lumen. The endoscope 11 may include the guide wire hole 27 by using a hollow member having a plurality of drilled holes. The hollow member can be called the guide wire lumen. Out of the guide wire lumens, particularly a tubular (tube-shaped) one is called the lumen tube 71. In the endoscope 11, the lumen tube 71 is used in a rear end of a long cylindrical holder 73 serving as the front end in the insertion direction. In this manner, the guide wire 25 is adapted to penetrate through the guide wire hole 27 of the lumen tube 71.

Figure 13:
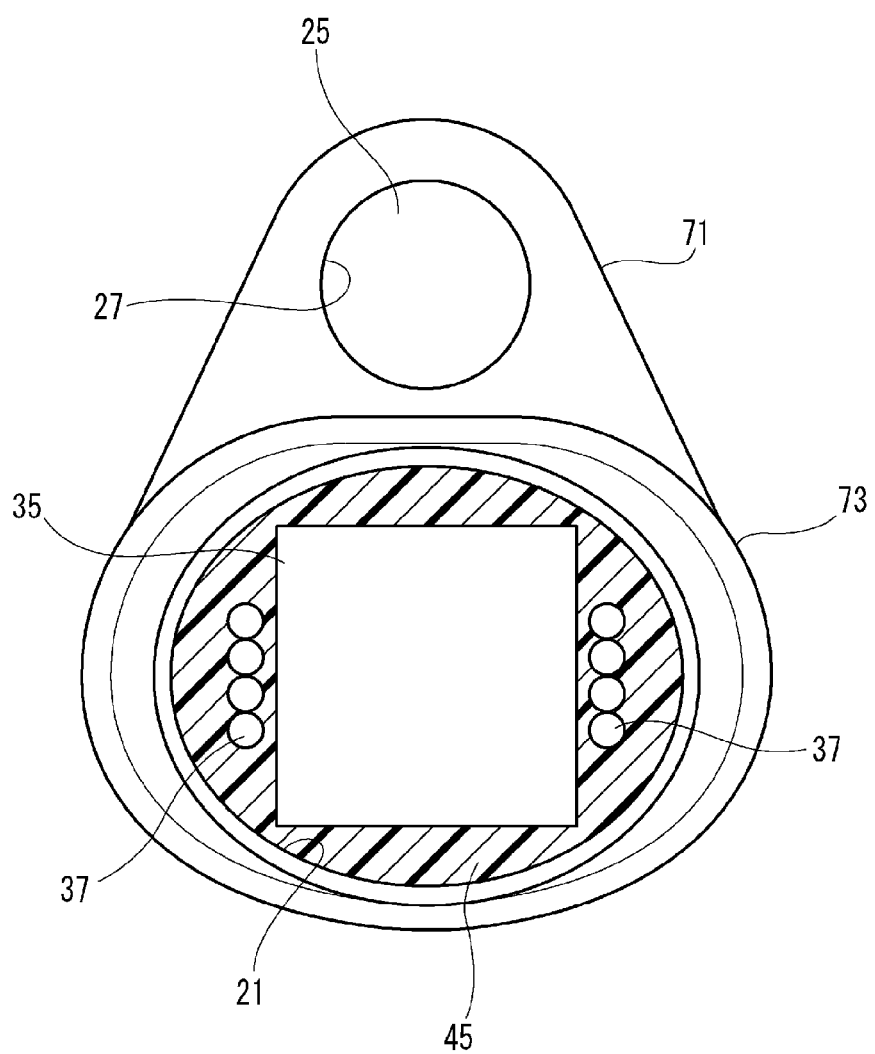
FIG. 13 is a front view of the lumen tube illustrated in FIG. 12.

FIG. 13 is a front view of the lumen tube 71 illustrated in FIG. 12. In this case, the holder 73 can adopt a simple structure having no ridge portion 41. The front end surface of the holder 73 has the observation hole 43 for arranging the lens cover glass 35 and the lighting optical fiber 37. The lens cover glass 35 and the lighting optical fiber 37 which are arranged inward of the observation hole 43 are stably fixed by using the black resin 45 filling the observation hole 43.

Figure 14:
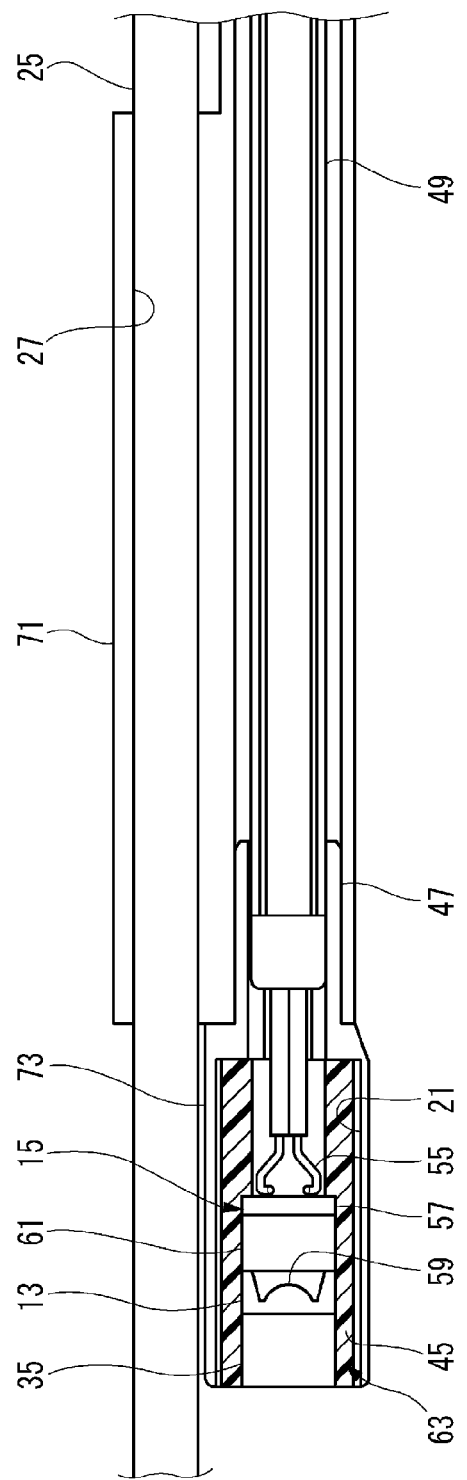
FIG. 14 is a side sectional view of FIG. 12.

FIG. 14 is a side sectional view of FIG. 12. If the endoscope 11 has a tubular portion equivalent to the sheath 19 and employs the lumen tube 71 in which the guide wire hole 27 is formed only in the front end in the insertion direction of the tubular portion, the sheath 19 can be omitted. In this manner, the holder 73 can be simplified.

In other words, in the endoscope 11 illustrated in FIGS. 1 to 9, the conductive member (that is, the holder 17) having the guide wire hole 27 also serves as the guide wire lumen. On the other hand, in the configuration using the lumen tube 71, the holder 73 can be simplified. However, a portion for forming the guide wire hole of the lumen tube 71 is lengthened, thereby causing poor bending performance. In contrast, according to the endoscope 11 in which the guide wire hole 27 is formed in the metal-made holder 17 described above, the total length of the holder 17 is shortened, thereby ensuring satisfactory bending performance.

Figure 15:
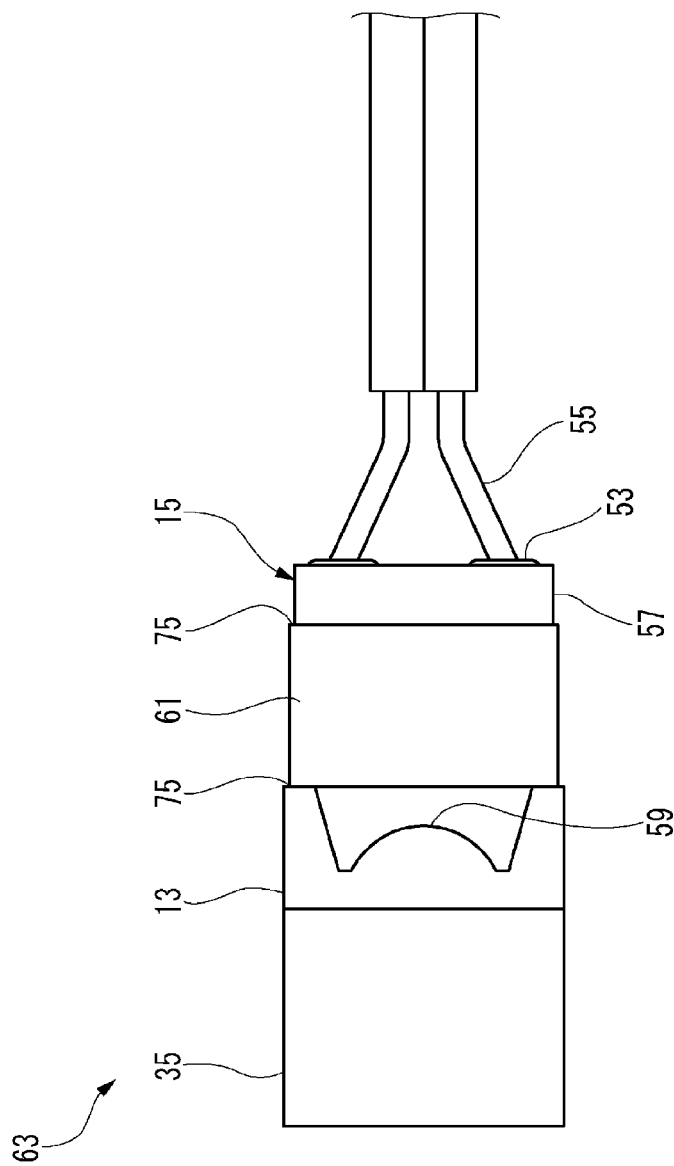
FIG. 15 is a side view of an imaging unit.

FIG. 15 is a side view of the imaging unit 63. In the imaging unit 63 of the endoscope 11, the lens 13 is integrally fixed to the light receiving surface of the image sensor 15. More specifically, the lens cover glass 35 and the lens 13 which are integrally formed in the same outer shape are fixed to the sensor cover glass 61 fixed to the light receiving surface of the image sensor 15. Here, in the imaging unit 63, each outer shape of the lens cover glass 35 and the lens 13 is formed to be larger than the sensor cover glass 61. Furthermore, the sensor cover glass 61 is formed to be larger than the outer shape of the sensor circuit unit 57 of the image sensor 15. That is, the lens 13, the sensor cover glass 61, and the sensor circuit unit 57 has each outer shape gradually decreasing via a step portion 75.

Figure 16:
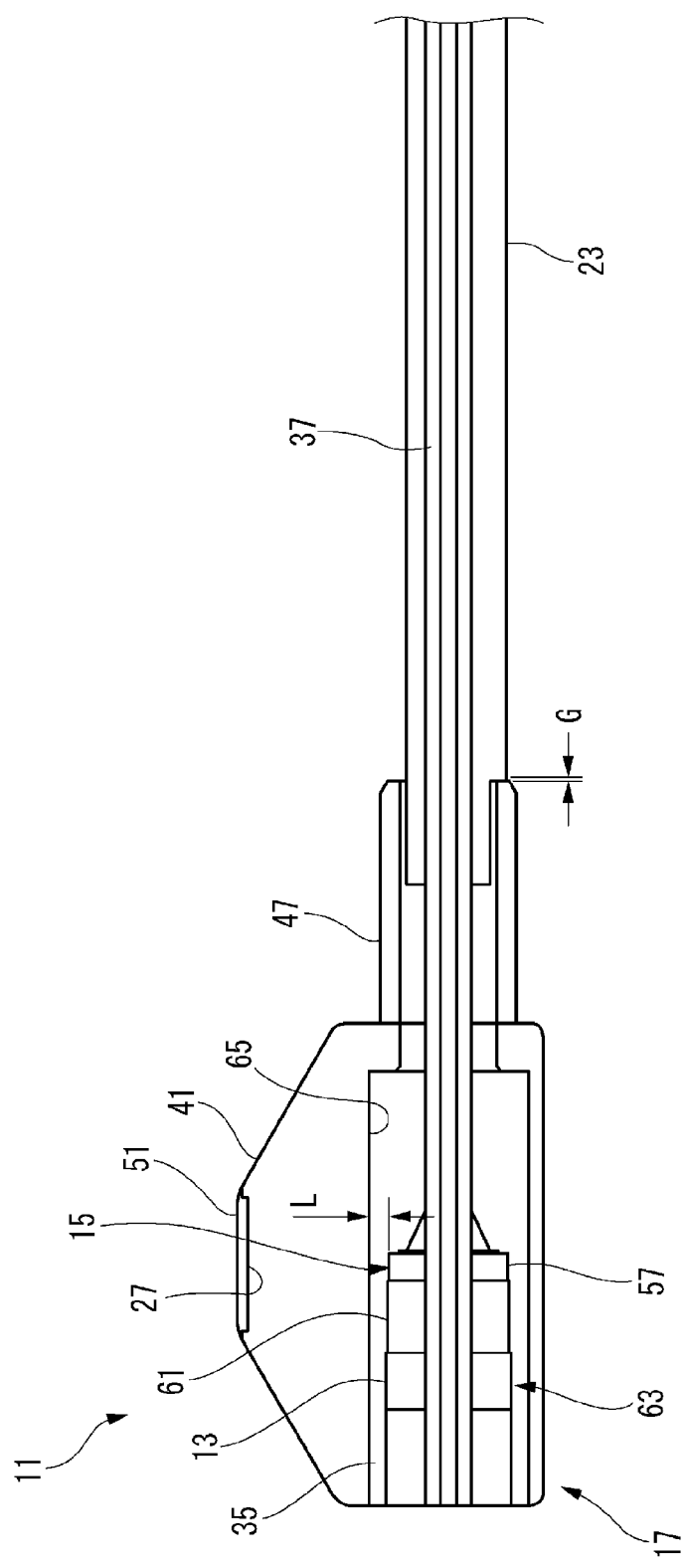
FIG. 16 is a side sectional view of the front end in the insertion direction of the endoscope, which shows an insulation structure of a sensor circuit unit.

FIG. 16 is a side sectional view of the front end in the insertion direction of the endoscope 11 which shows an insulation structure of the sensor circuit unit 57. In the endoscope 11, the sensor circuit unit 57 of the image sensor 15 is not in contact with the conductive member (inner surface of the holder 17).

In the endoscope 11, compared to insulation resistance (distance L) between the sensor circuit unit 57 and the conductive member (inner surface of the holder 17), insulation resistance (gap G) between the conductive member (sheath fitting portion 47) and the grounding member (metal wire 23) is smaller. That is, a dielectric breakdown distance between the holder 17 and the metal wire 23 is set to be shorter than a dielectric breakdown distance between the holder 17 and the sensor circuit unit 57 (L>G).

Next, an operation using the configuration of the endoscope 11 according to Embodiment 1 will be described.

The endoscope 11 according to Embodiment 1 has the lens 13 disposed in the front end in the insertion direction into the test object so that the imaging light is incident thereon. The endoscope 11 has the image sensor 15 connected to the rear end of the lens 13 and on which an image of the imaging light is formed. The endoscope 11 has the holder 17 covering the lens 13 and the image sensor 15 and having the guide wire hole 27 through which the guide wire 25 inserted into the test object penetrates. The endoscope 11 has the flexible tubular sheath 19 connected to the rear end portion of the holder 17 and into which the cable 49 conductively connected to the image sensor 15 is inserted.

In the endoscope 11 according to Embodiment 1, the sheath 19 is connected to the rear end portion of the holder 17. The sheath 19 is connected to the rear end portion of the holder 17. Accordingly, compared to a configuration in which the holder 17 is attached by covering the outer periphery of the sheath 19, the outer diameter can be formed to be smaller as much as the thickness of the sheath 19 on both sides in a diameter direction. Therefore, it is possible to prevent an increase in the maximum outer diameter of the endoscope. In addition, in the endoscope 11, the holder 17 disposed in the front end in the insertion direction houses both the lens 13 and the image sensor 15. Accordingly, compared to an imaging method of displaying a captured image by using the optical fiber bundle to guide the imaging light as in the related art, the captured image having higher quality can be obtained. Furthermore, the holder 17 of the endoscope 11 includes the guide wire hole 27. Therefore, the endoscope 11 can be easily inserted into a target site along the guide wire 25 by causing the guide wire 25 to penetrate through the guide wire hole 27.

Therefore, according to the endoscope 11 of Embodiment 1, in the configuration having both the lens 13 and the image sensor 15 in the front end and including the guide wire hole 27, the diameter can be reduced in the front end in the insertion direction.

In the endoscope 11, the holder 17 internally has the camera housing 65 for housing the lens 13 and the image sensor 15, and the front end of the sheath 19 is connected to the rear end of the camera housing 65.

In the endoscope 11, the front end of the sheath 19 is connected to the rear end of the camera housing 65. The front end in the insertion direction is configured to include the lens 13 and the image sensor 15, and the holder 17 covering both of these. In this manner, the holder 17 can form the camera housing 65 with a size which allows only minimum required configuration members to be housed. Therefore, the diameter and the size are easily reduced in the front end in the insertion direction in the endoscope 11.

In the endoscope 11, the holder 17 has the cylindrical sheath fitting portion 47 protruding rearward from the rear end of the camera housing 65. The front end of the sheath 19 is fitted and connected to the outer periphery of the sheath fitting portion 47.

In the endoscope 11, the camera housing 65 has the sheath fitting portion 47 protruding rearward from the rear end. The sheath fitting portion 47 is formed in a cylindrical shape. In the holder 17, the camera housing 65 and the sheath fitting portion 47 can be integrally formed. The inner periphery of the sheath 19 is fitted and fixed to the outer periphery of the sheath fitting portion 47. The sheath fitting portion 47 is formed to have such a size that the outer shape of the fitted sheath 19 does not protrude outward of the outer shape of the holder 17. For example, an adhesive is used in fixing the sheath 19 and the sheath fitting portion 47 to each other. The sheath fitting portion 47 is fitted to the outer periphery of the sheath fitting portion 47. Accordingly, a large adhesion area can be secured. In this manner, the sheath 19 and the holder 17 can ensure improved connection strength, compared to a connection structure in which the end surfaces but against each other. In addition, the large adhesion area can be secured. Therefore, waterproof performance can be improved in a joint portion between the holder 17 and the sheath 19.

The endoscope 11 has the elliptical shape in which the cross-sectional shape in the direction perpendicular to the axis line of the sheath fitting portion 47 has one end of the minor axis close to the guide wire hole 27.

In the endoscope 11, the cross-sectional shape of the sheath fitting portion 47 is an elliptical shape. Therefore, the cross-sectional shape of the sheath 19 fitted to the outer periphery of the sheath fitting portion 47 is also the elliptical shape, accordingly. In this elliptical shape, one end of the minor axis is oriented close to the guide wire hole 27. Therefore, below the guide wire 25 penetrating through the guide wire hole 27, the sheath 19 connected to the sheath fitting portion 47 deforms into a horizontally long elliptical shape. In this manner, the gap 67 is formed between the guide wire 25 and the sheath 19. In the endoscope 11, due to the gap 67, the guide wire 25 and the sheath 19 do not interfere with each other. A portion intermediately close to the rear end of the holder 17 is likely to be bent, thereby improving insertion performance. In addition, the dimension in the upward-downward direction of the sheath 19 is shortened. In this manner, the dimension of the outer diameter of the front end portion of the endoscope 11 can also be shortened.

The endoscope 11 penetrates through the guide catheter, and a clear liquid is caused to flow from the guide catheter into the blood vessel, thereby maintaining a visual field. In this case, the outer shape in a front view becomes a so-called teardrop shape. Therefore, it is possible to prevent a deviation in a discharge direction of the liquid.

In the endoscope 11, the holder 17 is made of metal (that is, formed using rigid metal).

In the endoscope 11, the guide wire 25 is caused to penetrate through the guide wire hole 27, and the holder 17 is inserted into the target site along the guide wire 25. In this case, compared to a case where the holder 17 is made of a resin or ceramic, it is possible to prevent abrasion of the guide wire hole 27 which is caused by sliding contact with the guide wire 25.

In the endoscope 11, the front end surface of the holder 17 has only two holes including the guide wire hole 27 and the observation hole 43 for arranging the lens 13 and the lighting optical fiber 37.

In the endoscope 11, the front end surface of the holder 17 has only the observation hole 43 in addition to the guide wire hole 27. The lens 13 and the lighting optical fiber 37 are arranged in the observation hole 43. In order to obtain a satisfactory lighting effect, a pair of the lighting optical fibers 37 is generally located across the lens 13. In a case where dedicated holes are formed in the holder 17, for example, four holes are required for the front end surface. It is desirable that a vascular endoscope caused to penetrate through the guide catheter (inner diameter of approximately 1.5 mm) has at least the outer diameter of 1.4 mm or smaller. If the four holes are formed on the thinned front end surface, the four holes can be obstacles in achieving manufacturing cost reduction and mass productivity of the holder 17. Therefore, in the endoscope 11, the lens 13 and the lighting optical fiber 37 are arranged in the same room serving as one observation hole 43. In this manner, the endoscope 11 eases a processing limit, reduces the manufacturing cost, and ensures the mass productivity. The observation hole 43 is filled with the black resin 45. The black resin 45 filling the observation hole 43 forms a partition wall for respectively dividing the lens 13 and the lighting optical fiber 37. In this manner, in the endoscope 11, illumination light is prevented from being incident on the lens 13 from the lighting optical fiber 37. In addition, the periphery of the lighting optical fiber 37 is coated black. Accordingly, it is possible to prevent the illumination light from being incident on the lens 13 from the lighting optical fiber 37. In this case, the resin used for the filling may not be black.

In a front view of the front end surface on which the guide wire hole 27 and the observation hole 43 are arranged up and down, the holder 17 is formed so that a lateral width across the guide wire hole 27 is narrower than a lateral width across the observation hole 43.

In the endoscope 11, the holder 17 is formed so that the lateral width across the guide wire hole 27 is narrower than the lateral width across the observation hole 43. That is, the holder 17 is formed in a so-called teardrop shape in a front view. As described above, the endoscope 11 penetrates through the guide catheter, and a clear liquid is caused to flow from the guide catheter into the blood vessel, thereby maintaining a visual field. In this case, the endoscope 11 has the teardrop shape. Accordingly, a sufficient gap can be secured between the endoscope 11 and the inner diameter of the guide catheter serving as a circumscribed circle. In this manner, the endoscope 11 can reliably secure a fluid discharge space, compared to a case where the holder 17 is a perfect circle in a front view.

The endoscope 11 has the lens 13 disposed in the front end in the insertion direction into the test object so that the imaging light is incident thereon. The endoscope 11 has the image sensor 15 connected to the rear end of the lens 13 and on which an image of the imaging light is formed. The endoscope 11 has the conductive member (for example, the holder 17 and the metal cylinder portion 21) covering the lens 13 and the image sensor 15. The endoscope 11 has the grounding member (for example, the metal wire 23) for grounding the above-described conductive member to the ground (GND).

In the endoscope 11, the conductive member covers the image sensor 15 disposed together with the lens 13 in the front end in the insertion direction. The conductive member is grounded to the ground (GND) via the grounding member. For example, the grounding member may be a metal braid of a blade tube in addition to the metal wire 23. The conductive member covering the lens 13 and the image sensor 15 allows the imaging light (that is, light reflected from an object such as a lesion in a test object) from ahead of the front end in the insertion direction to be incident thereon, and causes the grounding member to extend rearward in the insertion direction. Therefore, in the conductive member, the front end in the insertion direction and the rear end in the insertion direction are open. That is, the conductive member is cylindrical. For example, in a case where the conductive member is a cylinder, the conductive member can surround the image sensor 15 in all directions of 360 degrees around the axis line. In this manner, the image sensor 15 can be accurately shielded from the static electricity discharged in all directions of 360 degrees. In addition, the size of the endoscope 11 can be reduced, compared to a structure in which the insulation is performed by setting a sufficient space without providing the conductive member. As a result, according to the endoscope 11, operation reliability of the image sensor 15 can be improved while the reduced diameter is achieved.

Therefore, according to the endoscope 11 of Embodiment 1, the image sensor 15 can be protected from breakage caused by the static electricity while an increase in the diameter is prevented using a simple structure. Therefore, safe use can be ensured.

The image sensor 15 is surrounded by the conductive member. Accordingly, the static electricity is not discharged from the grounding member conductively connected to the end of the conductive member. Therefore, a bare lead wire whose insulation coating is omitted can be used for the grounding member. As a result, a configuration of the insulation coating is omitted from the outer periphery of the grounding member. Correspondingly, the diameter of the sheath 19 into which the grounding member is inserted can be reduced.

The endoscope 11 further has the guide wire lumen disposed in the front end in the insertion direction and having the guide wire hole 27 through which the guide wire 25 penetrates.

In the endoscope 11, the guide wire lumen is disposed in the front end in the insertion direction. In this case, the conductive member can be disposed inward of the guide wire lumen. The guide wire lumen may be made of a resin or metal. For example, the guide wire lumen can be the lumen tube 71 made of a flexible resin. The lumen tube 71 may be integrally formed with the sheath 19 connected to the rear end of the conductive member. The lumen tube 71 has the guide wire hole 27 through which the guide wire 25 penetrates. In the endoscope 11, the lumen tube 71, the conductive member, and the image sensor 15 are included in the front end in the insertion direction. In this manner, the endoscope 11 can obtain an observation image having high quality while the image sensor 15 is protected from the static electricity. In addition to this configuration, the endoscope 11 can be easily inserted into the target site along the guide wire 25 by causing the guide wire 25 to penetrate through the guide wire hole 27 of the lumen tube 71.

In the endoscope 11, the conductive member having the guide wire hole 27 also serves as the guide wire lumen.

In the endoscope 11, the guide wire hole 27 is formed in the conductive member. The conductive member having the guide wire hole 27 is equivalent to the above-described holder 17. That is, in the endoscope 11, the front end in the insertion direction is configured to employ the holder 17. In this manner, the lumen tube 71 can be omitted.

In the endoscope 11, the sensor circuit unit 57 of the image sensor 15 and the conductive member are not in contact with each other (that is, both of these are arranged apart from each other).

In the endoscope 11, the static electricity flowing to the grounding member and discharged to the conductive member can be prevented from causing a short circuit of the image sensor 15. In this manner, the image sensor 15 can be prevented from being broken or damaged due to the static electricity flowing to the sensor circuit unit 57.

In the endoscope 11, the lens 13 is integrally fixed so that an image of the imaging light (that is, light reflected from an object such as a lesion in a test object) is formed on the light receiving surface of the image sensor 15. In addition, the outer diameter of the outer shape (that is, a cross-sectional shape in the direction perpendicular to the optical axis of the lens 13) of the lens 13 is larger than the outer diameter of the outer shape (that is, a cross-sectional shape in the direction perpendicular to the optical axis of the lens 13) of the sensor circuit unit 57 of the image sensor 15.

In a manufacturing process of the endoscope 11, the lens 13 and the image sensor 15 which are integrated with each other are inserted into the conductive member, and are assembled together as the imaging unit 63. In this case, even if the imaging unit 63 comes into contact with the inner surface of the conductive member, the lens 13 comes into contact with the conductive member, and the sensor circuit unit 57 is less likely to come into contact with the inner surface of the conductive member. In this manner, at the time of mass production, productivity can be improved by reducing the risk that the sensor circuit unit 57 may come into contact with the conductive member.

In the endoscope 11, insulation resistance between the conductive member and the grounding member is smaller than insulation resistance between the sensor circuit unit 57 and the conductive member.

In the endoscope 11, the distance (gap G) between the conductive member and the grounding member is set to be smaller than the distance L between the sensor circuit unit 57 and the conductive member. It is not particularly difficult to conductively connect the conductive member and the grounding member to each other. If the conductive member and the grounding member are conductively connected to each other, a slight distance may be secured between the sensor circuit unit 57 and the conductive member. For example, if a space distance of 10 μm is secured, a withstand voltage of 200 V can be obtained. In this manner, a large current using a high voltage of the static electricity can be reliably supplied to the grounding member. Therefore, the image sensor 15 can be protected from breakage.

In the endoscope 11, the grounding member is the metal wire 23.

In the endoscope 11, the metal wire 23 is used as the grounding member. In this manner, it is possible to simultaneously obtain a grounding function of the conductive member and pushing ability (so-called pushability that is less likely to buckle) using the rigidity of the metal wire 23.

Hitherto, various embodiments have been described with reference to the drawings. However, as a matter of course, the present disclosure is not limited to the examples. It is obvious that various modifications, corrections, substitutions, additions, deletions, and equivalents within the scope disclosed in the appended claims are conceivable by those skilled in the art. It should be naturally understood that all of these belong to the technical scope of the present disclosure. In addition, the respective configuration elements in the various embodiments described above may be optionally combined with each other within the scope not departing from the gist of the invention.

The present disclosure is useful for the endoscope which has both the lens and the image sensor in the front end, which includes the guide wire hole, and which can be easily inserted along the guide wire while the diameter can be reduced in the front end in an insertion direction.

Other Embodiment

The present disclosure tries to solve another problem. Although an optical lens is disposed in a front end of the thinned vascular endoscope catheter disclosed in Japanese Registered Utility Model No. 3188206, an image sensor for capturing an image is not disposed in the front end. In consideration with a configuration in which an image sensor is disposed in an insertion front end of the endoscope so as to capture a high-quality image of an object (e.g., a lesion in a test object as being a human body) in which the endoscope is inserted, there is a problem that requires a minimization of the front end and a countermeasure against static electricity which considers avoidance of a damage such as a destruction of the image sensor due to the static electricity from the object.

Japanese Registered Utility Model No. 3188206 does not recognize such a problem.

The present disclosure is devised in view of the above-described circumstances in the related art, and also aims to provide an endoscope which can avoid larger diameter with a simple structure and prevent an image sensor from being damaged due to a static electricity.

According to the present disclosure, there may be provided another endoscope as follows.

(1) An endoscope including:

a lens which is disposed in a front end in an insertion direction into a test object, and receives an incident imaging light;

an image sensor which is disposed in a rear end of the lens, wherein an image of the imaging light is formed on the image sensor;

a conductive member which covers the lens and the image sensor; and a grounding member which grounds the conductive member.

(2) The endoscope according to the configuration (1), further including a guide wire lumen which is disposed in a front end in the insertion direction, wherein the guide wire lumen has a guide wire hole through which the guide wire penetrates.

(3) The endoscope according to the configuration (2), wherein the conductive member servers as the guide wire lumen having the guide wire hole.

(4) The endoscope according to any one of the configurations (1) to (3), wherein the a sensor circuit unit of the image sensor and the conductive member are arranged apart from each other.

(5) The endoscope according to the configuration (4), wherein the lens is arranged so that an image of the image light is formed on a light receiving surface of the image sensor, and an outer diameter of a cross-sectional shape in a direction perpendicular to the optical axis of the lens is larger than an outer diameter of a cross-sectional shape in a direction perpendicular to the optical axis of the sensor circuit unit.

(6) The endoscope according to the configuration (4), wherein insulation resistance between the conductive member and the grounding member is smaller than insulation resistance between the sensor circuit unit and the conductive member.

(7) The endoscope according to the configuration (6), wherein the grounding member is a metal wire.

This application is based upon and claims the benefit of priorities of Japanese Patent Applications No. 2018-133077 and No. 2018-133078 both filed on Jul. 13, 2018, the contents of which are incorporated herein by reference in its entirety.

The reference numerals and signs used in the present disclosure are listed below.
11: endoscope
13: lens
15: image sensor
17: holder
19: sheath
21: metal cylinder portion
23: metal wire
25: guide wire
27: guide wire hole
37: lighting optical fiber
43: observation hole
47: sheath fitting portion
49: cable
57: sensor circuit unit
65: camera housing

What is claimed is:

1. An endoscope comprising:
a lens configured to receive light reflected from an object;
an image sensor facing the lens, the image sensor configured to receive the light through the lens and capture an image of the object;
a holder including a first end, a second end opposite to the first end, a tubular sheath fitting portion at the second end, a column portion having an observation hole, and a ridge portion having a guide wire hole through which a guide wire to be inserted into a test object is able to penetrate, the guide wire hole positioned between the first and second ends of the holder, the lens and the image sensor positioned inside of the observation hole and aligned with each other along a first axis, the column portion and the ridge portion aligned with each other along a second axis transverse to the first axis, the lens positioned between the first end of the holder and the image sensor, the image sensor positioned between the lens and the second end of the holder, the ridge portion including:
a bridge portion;
an inclined surface extending from the first end of the holder to the bridge portion, the inclined surface having a first inclination angle relative to the first axis; and
a declined surface extending from the bridge portion to the second end of the holder, the declined surface having a second inclination angle relative to the first axis, the guide wire hole extending through the inclined surface and the declined surface;
a flexible tubular sheath physically coupled to the tubular sheath fitting portion; and
a cable inserted in the flexible tubular sheath, the cable being electrically coupled to the image sensor,
wherein a cross-sectional shape of the tubular sheath fitting portion extending along the second axis is an ellipse, and
the ellipse has a minor axis extending along the second axis such that a step is formed between an end of the declined surface and an outer surface of a portion of the flexible tubular sheath fitted to the tubular sheath fitting portion, and a gap is formed between the outer surface of the portion of the flexible tubular sheath and the guide wire along the second axis when the guide wire penetrates the guide wire hole.

2. The endoscope according to claim 1, wherein the holder internally includes a camera housing which houses the lens and the image sensor, and
wherein a front end of the flexible tubular sheath is connected to a rear end of the camera housing.

3. The endoscope according to claim 2, wherein the tubular sheath fitting portion protrudes rearward from the rear end of the camera housing, and
wherein the front end of the flexible tubular sheath is fitted and connected to an outer periphery of the tubular sheath fitting portion.

4. The endoscope according to claim 1, wherein the holder is formed of metal.

5. The endoscope according to claim 1, wherein
the guide wire hole has a first width extending along a third axis transverse to the first and second axes, and
the observation hole has a second width extending along the third axis that is larger than the first width.

6. The endoscope according to claim 1, wherein
the image sensor is positioned between the lens and the tubular sheath fitting portion.

7. The endoscope according to claim 1, further comprising:
resin in the observation hole, the lens being coupled to an inner surface of the column portion by the resin.

8. The endoscope according to claim 1, further comprising:
a grounding member in the flexible tubular sheath and coupled to the tubular sheath fitting portion, the holder being made of a conductive material.

9. The endoscope according to claim 1, further comprising:
a grounding member in the flexible tubular sheath;
a first gap between an inner surface of the column portion and the image sensor;
a second gap between the tubular sheath fitting portion and the grounding member, the first gap being larger than the second gap.

10. The endoscope according to claim 1, further comprising:
a conductive cylinder inside of the observation hole, the lens and the image sensor positioned inside of the conductive cylinder, the holder being made of a resin.

* * * * *